(12) United States Patent
Savino

(10) Patent No.: US 6,796,935 B1
(45) Date of Patent: Sep. 28, 2004

(54) MULTIPLE SEED IMPLANTER

(76) Inventor: Michael Savino, 71 Everett Ave., Staten Island, NY (US) 10309

( * ) Notice: Subject to any disclaimer, the term of this patent is extended or adjusted under 35 U.S.C. 154(b) by 0 days.

(21) Appl. No.: 10/392,718

(22) Filed: Mar. 20, 2003

(51) Int. Cl.[7] .............................. A61M 5/00; A61N 5/00
(52) U.S. Cl. ........................................... 600/7; 604/173
(58) Field of Search ............................ 600/1, 3, 7, 439; 604/19, 173

(56) References Cited

U.S. PATENT DOCUMENTS

| | | | | |
|---|---|---|---|---|
| 4,586,490 A | * | 5/1986 | Katz | 600/3 |
| 5,417,683 A | * | 5/1995 | Shiao | 606/1 |
| 5,683,345 A | * | 11/1997 | Waksman et al. | 600/3 |
| 6,575,890 B2 | * | 6/2003 | Kaplan et al. | 600/7 |
| 6,626,817 B2 | * | 9/2003 | Luth | 600/7 |
| 6,638,206 B2 | * | 10/2003 | Green et al. | 600/7 |
| 6,648,811 B2 | * | 11/2003 | Sierocuk et al. | 600/7 |

* cited by examiner

*Primary Examiner*—Eric F. Winakur
*Assistant Examiner*—Nikita R. Veniaminov

(57) ABSTRACT

The present invention is a seed implantation apparatus comprising a cartridge with an array of chambers having a plurality of hollow needles inside chambers, which can hold one or more radioactive seeds. The seed implantation apparatus also comprises pistons for each of the hollow needles and a plate located behind the pistons with a rod and a mechanical trigger, wherein said actuation causes said plate to move said pistons into said needles. The present invention also includes a method of using the seed implantation apparatus. The apparatus can be used in connection with brachytherapy and has particular utility in connection with simultaneously injecting multiple radioactive seeds into the prostate.

12 Claims, 3 Drawing Sheets

MULTIPLE SEED IMPLANTER

BACKGROUND OF THE INVENTION

1. Field of the Invention

The present invention relates to a seed implanter for use in connection with brachytherapy. The seed implanter has particular utility in connection with simultaneously injecting multiple radioactive seeds into the prostate.

2. Description of the Prior Art

The implantation of radioactive seeds into the prostate, or brachytherapy, is an effective treatment for prostate cancer. This is commonly accomplished by loading radioactive seeds into hollow needles and inserting the needles into the prostate. The radioactive seeds are either injected singly, with the physician manually placing each seed in the prostate, or they are injected as a string with two or more seeds spaced apart.

The use of implantation devices for brachytherapy is known in the prior art. Commonly, a hollow needle is loaded and placed over the injection site of a patient. A piston or stylet is then used to push the radiation source into the desired area in the patient.

U.S. Pat. No. 5,683,345 to Waksman discloses a method and apparatus for delivery of a radiation source to a tumor. However, Waksman's patent provides only a single catheter for delivery of one radiation source at a time. To provide an array of radiation sources to a tumor, the device must be reloaded and repositioned.

Implantation needles have been used with a grid or template to aid in the accurate placement in the prostate. One example of such a grid is the SeedNut™ that is used for increasing accuracy and control in tumor ablation.

There are no patents disclosing multiple needles that can be triggered simultaneously for the injection of multiple seeds at multiple sites in a solid mass tumor. Therefore, a need exists for a new and improved seed implantation device that can be used for brachytherapy. In this regard, the present invention substantially fulfills this need. In this respect, the seed implantation device according to the present invention substantially departs from the conventional concepts and designs of the prior art, and in doing so provides an apparatus primarily developed for the purpose of providing a rapid and simple means of providing an array of radiation sources to a solid mass tumor.

SUMMARY OF THE INVENTION

In view of the foregoing disadvantages inherent in the known types of devices for brachytherapy now present in the prior art, the present invention provides an improved seed implantation device, and overcomes the above-mentioned disadvantages and drawbacks of the prior art. As such, the general purpose of the present invention, which will be described subsequently in greater detail, is to provide a new and improved seed implantation device and method of use which has all the advantages of the prior art mentioned heretofore and many novel features. This results in a seed implantation device that is not anticipated, rendered obvious, suggested, or even implied by the prior art, either alone or in any combination thereof.

To attain this, the present invention essentially comprises a seed implantation apparatus having a seed cartridge along with an array of hollow needles adapted for accepting radioactive seeds with each of said hollow needles having a piston, a plate located behind the pistons, a rod and a mechanical trigger capable of actuating a rod, wherein actuation causes ejection of seeds from the apparatus.

There has thus been outlined, rather broadly, the more important features of the invention in order that the detailed description thereof that follows may be better understood and in order that the present contribution to the art may be better appreciated.

There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. In addition, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved seed implantation device that has all of the advantages of the prior art mentioned above and none of the disadvantages.

It is another object of the present invention to provide a new and improved seed implantation device that may be easily and efficiently manufactured and marketed.

An even further object of the present invention is to provide a new and improved seed implantation device that has a low cost of manufacture with regard to both materials and labor, and which accordingly is then susceptible of low prices of sale to the consuming public, thereby making such seed implantation device economically available to the buying public.

Still another object of the present invention is to provide a new seed implantation device that provides in the apparatuses and methods of the prior art some of the advantages thereof, while simultaneously overcoming some of the disadvantages normally associated therewith.

Even still another object of the present invention is to provide a seed implantation device that consists of multiple needles which can be triggered simultaneously for the injection of multiple seeds at multiple sites in a solid mass tumor, thus providing a rapid and simple means of providing an array of radiation sources to a solid mass tumor. In a specific embodiment the new and improved seed implantation device of the present invention can be used for brachytherapy. This allows the operator to insert multiple seeds in a pattern simultaneously.

Furthermore, it is an object of the present invention to provide a new and improved method for implanting radioactive seeds in a patient comprising loading a plurality of radioactive seeds into an apparatus, wherein said apparatus comprises two or more needles wherein said hollow needles are aligned in an array of two or more chambers. Additionally said array is used to guide the hollow needles of the apparatus to a desired location for the injection of a predetermined number of seeds into said patient, wherein all seeds are injected simultaneously.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE PREFERRED EMBODIMENT

Figure 2:
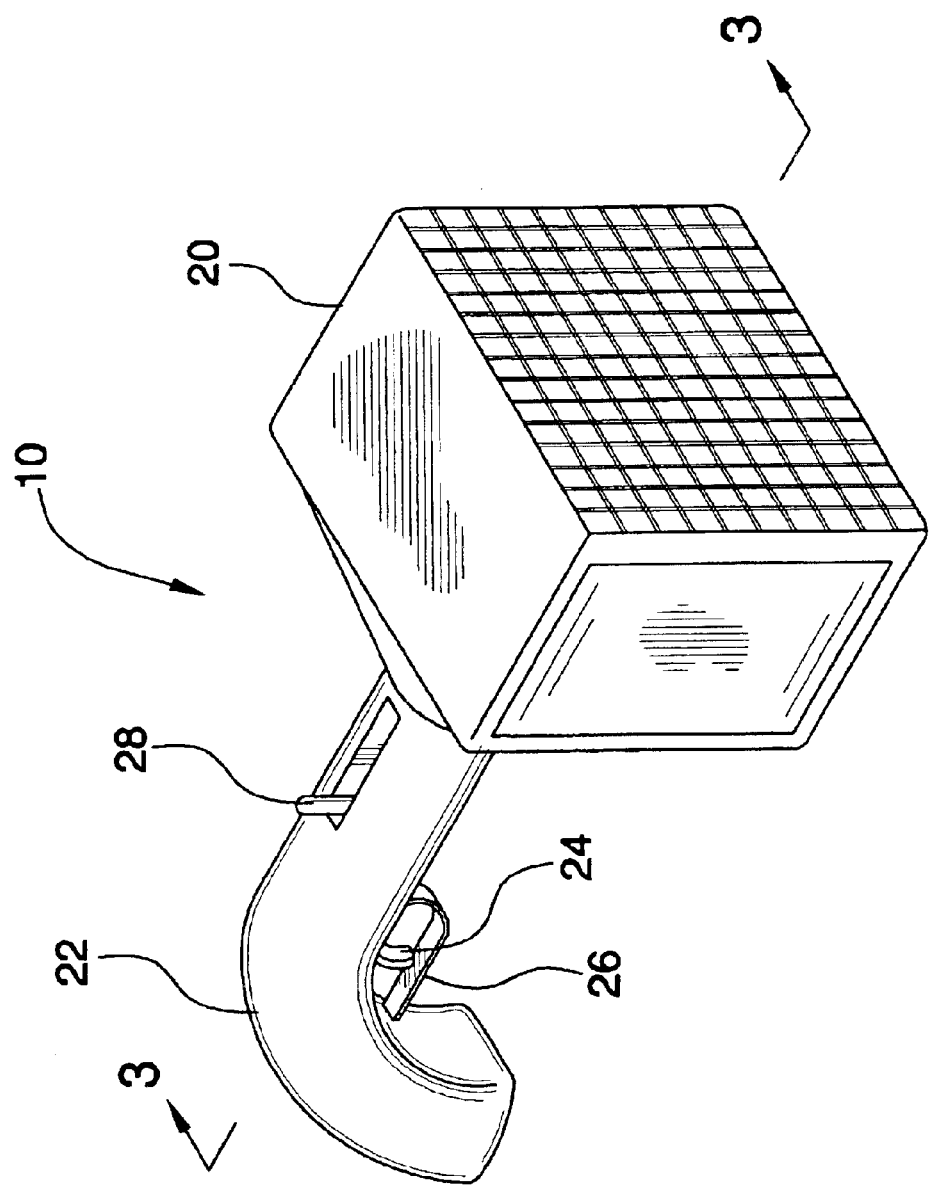
FIG. 2 is a perspective view of the seed implantation device constructed in accordance with the principles of the present invention.
Figure 3:
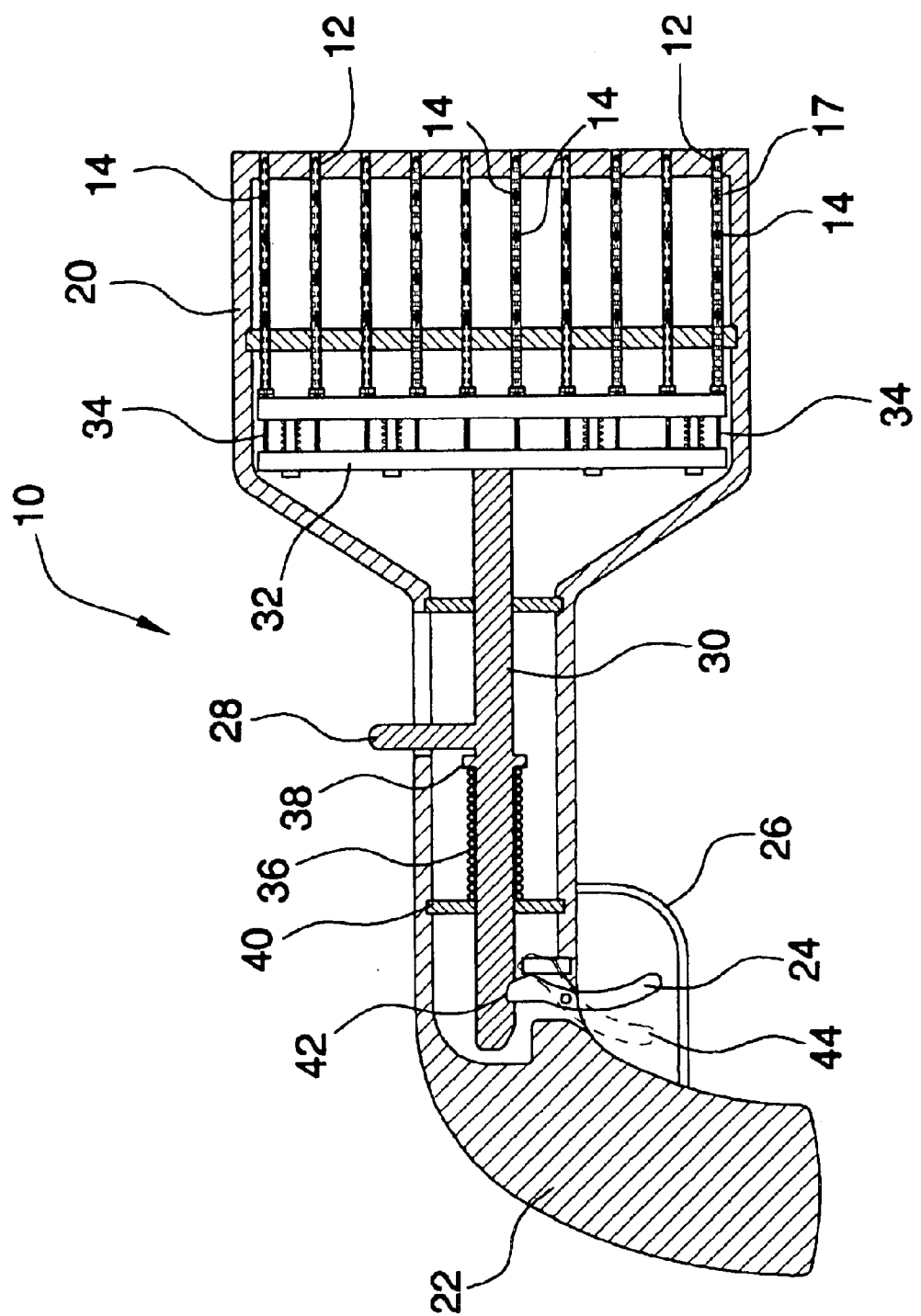
FIG. 3 is a cross-sectional view of the seed implantation device of the present invention.

Referring now to the drawings, and particularly to FIGS. 2–3, a preferred embodiment of the seed implantation device of the present invention is shown and generally designated by the reference numeral 10.

Figure 1:
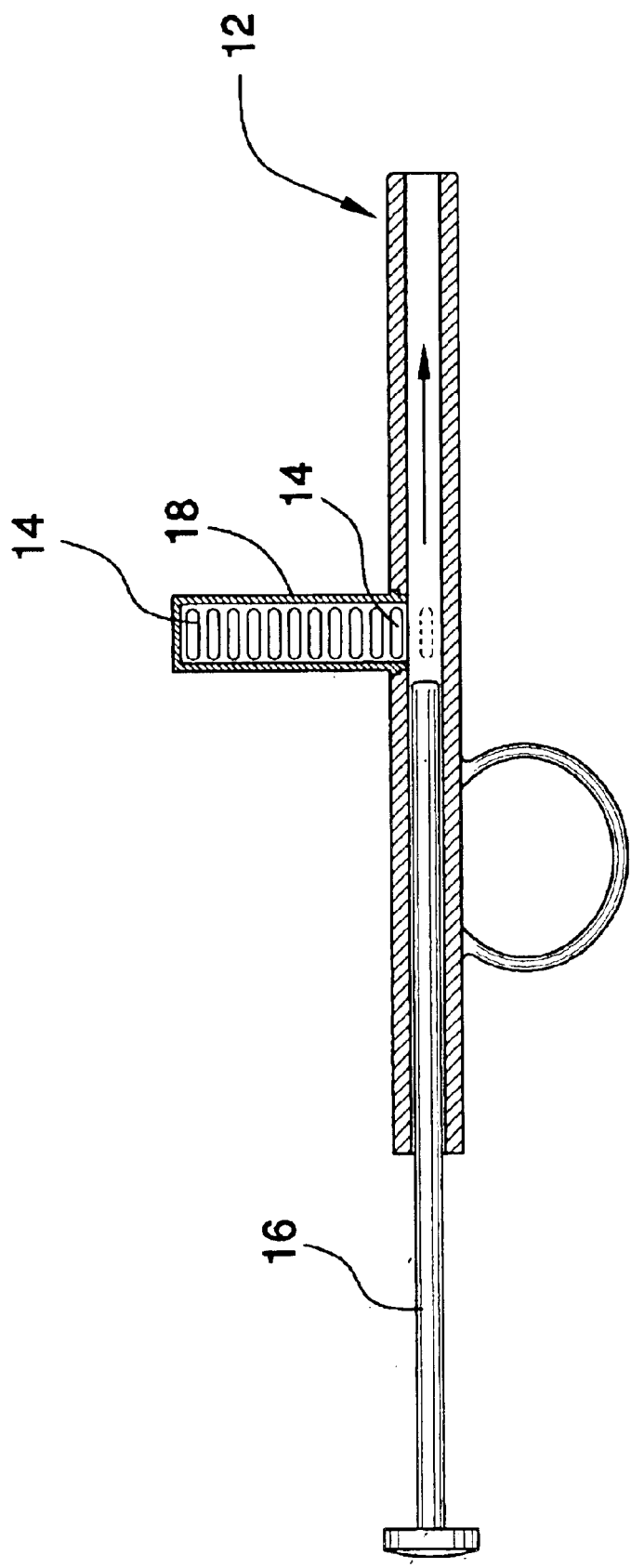
FIG. 1 is a cross-sectional view of the prior art seed implantation device.

A discussion of the prior art seed implantation device, which can be seen in FIG. 1, is warranted. The device comprises a single hollow needle 12 into which a radioactive seed 14 is loaded. When the needle 12 is placed over the solid mass tumor, the user pushes the piston 16 and injects the seed 14 into the tumor. The user can then load another seed 14 from a seed reservoir 18, reposition the device, and inject a second seed.

FIG. 2 illustrates a new and improved seed implantation device 10 of the present invention that is particularly useful for brachytherapy. More particularly, the seed implantation device 10 has a cartridge 20 for holding an array of hollow needles 12 and injecting a plurality of seeds simultaneously.

The cartridge 20 shown in FIG. 2 has enough chambers to accommodate 150 needles. However, smaller or larger arrays are also contemplated for use in accordance with smaller and larger tumors and density of seeds required during a procedure. These arrays are removable from the rest of the implantation device to allow for loading and reloading the arrays with hollow needles and seeds. The array may be square, rectangular, circular, or oval, depending upon the tumor.

All chambers in the cartridge may be filled with hollow needles for injecting radioactive seeds. Alternatively, some of the chambers may be left vacant for a lower density or smaller sized tumor. For example a limited number of needles 12 may be placed in the array 20 when fewer seeds 14 are needed for brachytherapy. The number and location of both needles 12 and seeds 14 can be determined prior to the implantation surgery and loaded into the seed implantation device 10 before the injection procedure. This reduces the time required by the doctor to complete the operation.

Each needle 12 can be loaded with one or more radioactive seeds 14 in the conventional fashion. The device 10 has a handle 22 and a trigger 24 that is compressed to inject the seeds 14 into the target. Additionally, a trigger guard 26 is provided to prevent accidental trigger activation. Furthermore a hammer 28 is located on the device for cocking the trigger 24 to enable the trigger for injecting the seeds. The handle 22 can consist of a form that is ergonomically designed to give the instrument maximum comfort and stability in a user's hand.

The location of the cut-away view of the seed implantation device 10 shown in FIG. 3 is indicated by the arrows and number 3s in FIG. 2. In this embodiment, array 20 shows ten hollow needles 12 filled with radioactive seeds 14. Several seeds 14 are loaded into each hollow needle 12 with optional spacing 17 between each seed 14.

When the trigger 24, protected by guard 26, is pulled back as indicated by the dotted outline of the trigger 44, an interior rod 30 is pushed forward and in turn moves plate 32 and pistons 34 forward, which in turn moves hollow needles 14 forward into the tumor resulting in the implanting multiple seeds 14 into the tumor.

The trigger 24 shown is an actuated, spring-loaded mechanism with springs 36 located behind the hammer 28 as shown in FIG. 3. The spring 36 is wrapped around interior rod 30 and held in place by notch 38 and plate 40. The spring is compressed by moving hammer 28 to the position whereby notch 42 in interior rod 30 locks trigger 24 in a ready position for firing. Once trigger 24 is pulled back to the dotted trigger position 44 the interior rod 30 is free to move forward due to the spring 36 uncompressing and pushing interior rod 30 forward and initiating the process of injecting the seeds 14 into a tumor. Alternatively, the trigger 24 may be an air activated trigger or any other form of triggering mechanism having similar effect.

Multiple seeds may be inserted into a single needle to provide a three dimensional array of seeds which are injected into a tumor to create a three dimensional array of radioactive seeds within the tumor whose relative positions were predetermined. The seeds may be connected to each other by a string or suture, and may be separated from each other by a spacer element. An example of a suture filled with spaced seeds is described in U.S. Pat. No. 6,264,600, herein incorporated by reference.

The radioactive seed may be made from any radioactive isotope known in the art for brachytherapy. Isotopes may be selected from, for example, $^{90}$yttrium $^{192}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{52}$iron, $^{32}$phosporous, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsnic, $^{103}$palladium, $^{203}$lead, $^{111}$indium, $^{167}$thaulium, $^{57}$nickel, $^{62}$zinc, $^{61}$copper $^{201}$thallium, or $^{123}$iodine. Preferable radioactive material for injection using the device of this invention include $^{198}$iridium, $^{198}$gold, $^{125}$iodine, $^{137}$cesium, and $^{60}$cobalt, depending on the size and type of tumor to be treated.

The device is used for treating any solid mass tumor. A solid mass tumor is defined as a cancerous or non-cancerous condition manifested by a solid mass growth as opposed to conditions lacking a solid growth such as leukemia. Various types of solid mass tumors may be treated with the device and methods of the current invention including both cancerous and benign tumors. Examples of cancerous solid mass tumors that may be treated include, for example, prostate cancer, lung cancer, cervical cancer, soft tissue sarcomas, kidney tumors and liver tumors. Examples of non-cancerous solid mass tumors that may be treated include, for example, brain tumors and uterine fibroid tumors.

In use, it can now be understood that the seed implantation device of the current invention can be used to inject an array of radioactive seeds at one time. The device may be pre-loaded, which substantially reduces the time required in an operating room. Instead of individually loading each seed, locating the implantation device at a specified spot above the solid mass tumor, and injecting each seed individually, the operator can locate the entire array of seeds above the solid mass tumor and inject all the seeds simultaneously. When large numbers of radioactive seeds need to be located in a tumor, this reduces the time and therefore the cost of the procedure considerably.

While a preferred embodiment of the seed implantation device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy and biocompatible material such as another metal or plastic may be used instead of the metal described. In addition, although seed implantation for brachytherapy has been described, it should be appreciated that the seed implantation device herein described is also suitable for any other technique where it is necessary to implant a solid or liquid material in a variety of places in a pattern that can be predetermined.

As used herein, the terms "approximately" and "about" means within 25% of the stated value, or more preferentially within 15% of the value. As used herein in the claim(s), when used in conjunction with the word "comprising", the words "a" or "an" may mean one or more than one. As used herein "another" may mean at least a second or more.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A seed implantation apparatus comprising:
   a cartridge comprising an array of chambers;
   a plurality of hollow needles inside said chambers, wherein said needles are adapted for holding one or more radioactive seeds, each of said hollow needles having a piston;
   a plate located behind said pistons;
   a rod located behind said plate;
   a mechanical trigger capable of actuating said rod, wherein actuation causes said plate to move said pistons into said needles and thereby eject one or more seeds from each of said needles; and
   a seed cartridge adapted for holding a plurality of radioactive seeds and delivering said seeds to said hollow needles.

2. A seed implantation apparatus comprising:
   a cartridge comprising an array of chambers, wherein said cartridge is removable;
   a plurality of hollow needles inside said chambers, wherein said needles are adapted for holding one or more radioactive seeds, each of said hollow needles having a piston;
   a plate located behind said pistons;
   a rod located behind said plate; and
   a mechanical trigger capable of actuating said rod, wherein actuation causes said plate to move said pistons into said needles and thereby eject one or more seeds from each of said needles.

3. A seed implantation apparatus comprising:
   a cartridge comprising an array of chambers wherein said cartridge is reloadable;
   a plurality of hollow needles inside said chambers, wherein said needles are adapted for holding one or more radioactive seeds, each of said hollow needles having a piston;
   a plate located behind said pistons;
   a rod located behind said plate; and
   a mechanical trigger capable of actuating said rod, wherein actuation causes said plate to move said pistons into said needles and thereby eject one or more seeds from each of said needles.

4. A method of implanting radioactive seeds in a patient comprising:
   loading a plurality of radioactive seeds into an apparatus, wherein said apparatus comprises:
      a cartridge comprising an array of chambers;
      a plurality of hollow needles inside said chambers, wherein said needles are adapted for holding one or more radioactive seeds, each of said hollow needles having a piston;
      a plate located behind said pistons;
      a rod located behind said plate; and
      a trigger capable of actuating said rod, wherein actuation causes said plate to move said pistons into said needles;
   using said cartridge to guide said needles of said apparatus to a desired location; and actuating said trigger which injects said plurality of seeds into said patient.

5. The method of claim 4, wherein all seeds are injected simultaneously.

6. The method of claim 4, further comprising sterilizing said apparatus before loading said seeds.

7. The seed implantation apparatus of claim 4, wherein the size of the template/grid is determined by the size of a solid mass tumor in said patient.

8. The method of claim 7, wherein said array of hollow needles is placed into the prostate of a male patient.

9. The method of claim 7, further comprising determining site for said array to be placed prior to implanting said seeds.

10. The method of claim 4, wherein said actuation of said trigger has spring action mechanism.

11. The method of claim 4, wherein said actuation of said trigger has an air release mechanism.

12. A method of implanting radioactive seeds in a patient comprising:
   loading a plurality of radioactive seeds into an apparatus, wherein said apparatus comprises:
      a cartridge comprising an array of chambers;
      a plurality of hollow needles inside said chambers, wherein said needles are adapted for holding one or more radioactive seeds, each of said hollow needles having a piston;
      a plate located behind said pistons;
      a rod located behind said plate; and
      a trigger capable of actuating said rod, wherein actuation causes said plate to move said pistons into said needles;
   using said cartridge to guide said needles of said apparatus to a desired location actuating said trigger which injects said plurality of seeds into said patient and wherein said seeds are selected from the group consisting of $^{198}$iridium, $^{198}$gold, $^{125}$iodine, $^{137}$cesium, and $^{60}$cobalt.

* * * * *